United States Patent [19]

Igaki et al.

[11] Patent Number: 5,017,710

[45] Date of Patent: May 21, 1991

[54] FLUORAN COMPOUND AND COLORING RECORDING MATERIAL USING IT

[75] Inventors: Tetsuo Igaki; Akio Kaneko; Sumio Manaka; Kimiaki Kinoshita, all of Tokyo, Japan

[73] Assignee: Nippon Soda Co., Ltd., Tokyo, Japan

[21] Appl. No.: 444,130

[22] PCT Filed: Mar. 13, 1989

[86] PCT No.: PCT/JP89/00270

§ 371 Date: Oct. 24, 1989

§ 102(e) Date: Oct. 24, 1989

[87] PCT Pub. No.: WO89/08656

PCT Pub. Date: Sep. 21, 1989

[30] Foreign Application Priority Data

Mar. 16, 1988 [JP] Japan ................. 63-62515

[51] Int. Cl.$^5$ ................... C07D 493/10; C09B 11/28; C07C 101/78
[52] U.S. Cl. .................. 549/226; 549/225; 562/441; 503/217; 503/221; 503/225
[58] Field of Search ............ 549/225, 226; 503/221, 503/217, 225; 562/441

[56] References Cited

U.S. PATENT DOCUMENTS

| | | | |
|---|---|---|---|
| 3,681,390 | 8/1972 | Lin | 549/225 |
| 3,681,392 | 8/1972 | Kimura et al. | 549/225 |
| 3,691,203 | 9/1972 | Koga et al. | 549/225 |
| 3,730,755 | 5/1973 | Lin | 549/225 |
| 4,410,708 | 10/1983 | Yahagi et al. | 549/226 |
| 4,515,971 | 5/1985 | Schmidt et al. | 549/225 |
| 4,536,220 | 8/1985 | Kondo et al. | 549/225 |
| 4,603,202 | 7/1986 | Mayer et al. | 549/225 |
| 4,612,558 | 9/1986 | Anzai et al. | 549/226 |
| 4,629,800 | 12/1986 | Yonese et al. | 549/225 |
| 4,694,088 | 9/1987 | Kaneko et al. | 549/226 |
| 4,728,633 | 3/1988 | Satomura et al. | 549/225 |
| 4,806,657 | 2/1989 | Zink | 549/226 |
| 4,837,210 | 6/1989 | Dwyer-Hallquist et al. | 549/226 |

FOREIGN PATENT DOCUMENTS

| | | |
|---|---|---|
| 112710 | 7/1984 | European Pat. Off. |
| 23204 | 7/1976 | Japan |
| 157153 | 9/1984 | Japan |
| 35053 | 2/1985 | Japan |
| 91258 | 5/1986 | Japan |

*Primary Examiner*—Cecilia Shen
*Attorney, Agent, or Firm*—George B. Oujevolk; Joseph C. Mason, Jr.

[57] ABSTRACT

Fluoran compounds represented by the general formula (I)

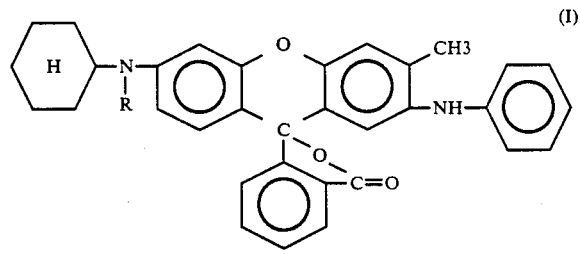

(where R is an alkyl group having 9 to 12 carbon atoms) and coloring recording materials containing the said compounds as coloring components, and benzoic acid derivatives represented by the general formula (II)

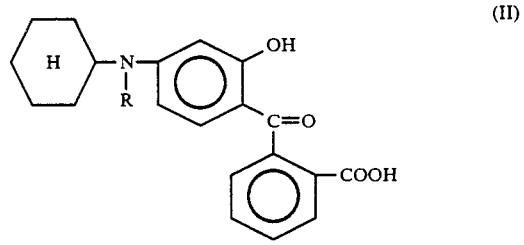

(where R is an alkyl group having 9 to 12 carbon atoms).

2 Claims, 3 Drawing Sheets

FLUORAN COMPOUND AND COLORING RECORDING MATERIAL USING IT

TECHNOLOGICAL FIELDS

This invention relates to new fluoran compounds and coloring recording materials with the said compound as coloring component, and to new intermediates useful for the syntheses of fluoran compounds.

BACKGROUND TECHNOLOGY

Coloring recording materials based on a coloring system consisting of a coloring dye which gives rise to a color by an action of developer though itself is colorless or has almost no color (hereinafter referred to "coloring dye") and a developer coloring the dye are used for, for instance, pressure sensitive copying paper, thermographic recording paper, prepaid cards or POS (point of sales) labels. Their applications are expanding.

A large number of proposals have been offered with regard to fluoran compounds as coloring dyes used for these coloring recording materials, and the fluoran compounds are used in a large amount in the market as well.

Out of the fluoran compounds, those having an anilino group at the 2 position and a methyl group at the 3 position as substituents and a substituted amino group at the 6 position are important as black coloring dyes, are a mainstream of the current market, and have a large number of proposals. That is, compounds having all alkyl groups for all the substituents of the said substituted amino group were proposed in U.S. Pat. No. 3,681,390, etc. Compounds having a cyclohexyl group and lower alkyl group as the substituents of the said substituted amino group are proposed in U.S. Pat. No. 4,410,708, etc. Compounds having a cyclohexyl group and an alkyl group having 5 to 8 carbon atoms are proposed in Japanese open patent No. Sho 60-35053.

However, the coloring performance of these known fluoran coloring dyes is not satisfactory yet. Particularly the improvement of the storability of the dyes is very desired.

The object of this invention is to provide coloring dyes with excellent coloring performance and storability, or coloring dyes with excellent solvility required when used for pressure sensitive copying paper.

DISCLOSURE OF THE INVENTION

This invention is a fluoran compound represented by the general formula (I)

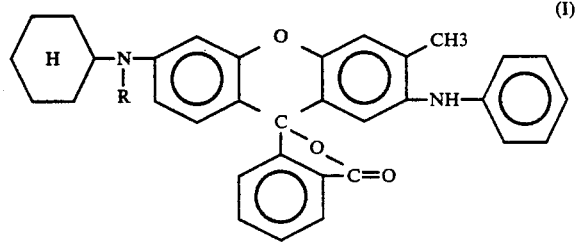

(I)

(where R is an alkyl group having 9 to 12 carbon atoms) and a coloring recording mataerial containing the said fluoran compound as a coloring dye.

In the fluoran compound represented by the general formula (I), R is a nonyl, decyl, undecyl or dodecyl group.

The fluoran compound represented by the general formula (I) is prepared in a way that a benzoic acid derivative represented by the general formula (II)

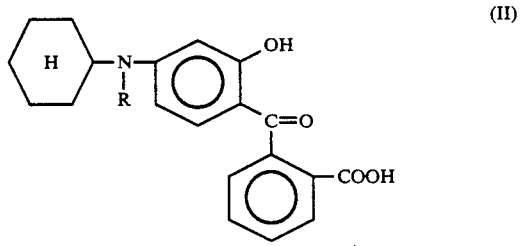

(II)

(where R is as defined above) is reacted with a derivative represented by the following formula

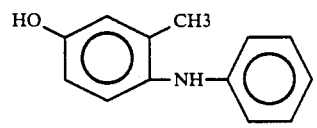

of which phenol or phenolic hydroxide group is converted to a lower alkoxy group such as methoxy or ethoxy group, at a molar ratio of about 1:1 in sulfuric acid. The concentration of sulfuric acid used is preferably 80% or more, and the intended product can be obtained by reaction at 0° to 50° C. for several to several 10 hours.

Concrete examples of fluoran compounds thus obtained and represented by the general formula (I) are listed in Table 1.

TABLE 1

| Compound | R | Melting point (°C.) | Color |
| --- | --- | --- | --- |
| No. 1 | n-C$_9$H$_{19}$ | 159–161 | a little reddish black |
| No. 2 | n-C$_{10}$H$_{21}$ | 135–138 | a little reddish black |
| No. 3 | n-C$_{12}$H$_{23}$ | 114–117 | a little reddish black |

The compounds of this invention have superior coloring sensitivity and superior property of less staining on the background, when compared with known analog compounds. Particularly compounds represented by the general formula (I) in which R has 10 or 12 carbon atoms have extremely high coloring sensitivity and extremely high solubility in organic solvents, being preferable compounds.

The fluoran compounds of this invention can of course be used singly to manufacture recording materials coloring black. In addition, two or more of the compounds can be used by mixing or the compound can be used by mixing with other coloring dyes: for instance, the fluoran compound is used by mixing with a coloring dye coloring black, red, blue, green, etc so that the black tone can be varied.

Coloring dyes applicable by mixing with the fluoran compound of this invention include compounds of fluoran, triphenylmethane-phthalide, phenothiazine spiropyrane and rhodamine lactam, and in addition coloring dyes with absorption in the near infrared region, which are attracting attention in recent years, including such compounds as triphenylmethane-phthalide, thiofluoran, fluoren and fluoran.

The coloring recording materials manufactured by using the fluoran compounds of this invention or a mixture of the fluoran compound with other coloring dyes are applicable to heat sensitive recording paper, which is the main application of the material, as well as pressure sensitive copying paper in addition to, for example, recording paper by thermographic transfer, electrothermo sensitive recording paper, electronic photographs using toner containing an acidic compound as a developer, ultrasonic recording paper, photosensitive printing materials, electron beam recording paper, materials for stamping, stamp ink, and typewriter ribbon.

Methods for the preparation of heat sensitive recording paper using the fluoran compounds of this invention are similar to those for existing coloring dyes: for example, fine particle of a fluoran compound of this invention or a mixture of it with other coloring dyes and fine particle of developer are dispersed in an aqueous solution of water-soluble binder, the resulting suspension is applied on paper to dry so as to give heat sensitive recording paper with excellent coloring property. An addition of sensitizer into the said suspension gives in heat sensitive recording paper with extremely high sensitivity. The suspension may additionally contain a filler, dispersant, colored image stabilizer, antioxidant, desensitizing agent, adhesion preventive agent, defoaming agent, light stabilizer, and optical whitening agent.

When doing so, developers used include bisphenol compounds such as bisphenol A, 4,4'-secondary butylidene bisphenol, 4,4'-cyclohexylidene bisphenol, 2,2'-dihydroxy diphenyl and pentamethylene-bis(4-hydroxybenzoate); bisphenol compounds containing sulfur such as 1,7-di(4-hydroxyphenyl thio)-3-dioxaheptane; 4-hydroxy benzoates such as benzyl 4-hydroxybenzoate, ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxybenzoate and diphenylmethyl 4-hydroxybenzoate; metal benzoates such as zinc benzoate and zinc 4-nitrobenzoate; hydroxy sulfones such as 4-hydroxy-4'-methyl diphenyl sulfone, 4-hydroxy-4'-isopropoxy diphenyl sulfone and 4-hydroxy-4'-butoxy diphenyl sulfone; 4-hydroxy phthalic acid diesters such as dimethyl 4-hydroxyphthalate, dicyclohexyl 4-hydroxyphthalate and diphenyl 4-hydroxyphthalate; esters of hydroxynaphthoic acid such as 2-hydroxy-6-carboxynaphthalene; hydroxyacetophenone, p-phenylphenol, benzyl 4-hydroxyphenylacetate, p-benzyl phenol, hydroquinone-monobenzyl ether; and tribromomethylsulfones such as tribromomethylphenyl sulfone.

Sensitizers used include higher fatty acid amides, benzamide, stearic acid anilide, acetoaceanilide, thioacetoanilide, dimethylphthalate, dibenzylterephthalate, dibe nzylisophthalate, bis (tert-butylphenol)s, bisphenol S diethers such as 4,4'-dimethoxy diphenyl sulfone, 4-iso-propoxy-4'-n-butoxydiphenyl sulfone, 4,4'-dibutoxydiphenyl sulfone and 4,4'-di-n- (or iso) pentyloxydiphenyl sulfone; diphenyl amine, carbazol, 2,3-di-m-tolylbutane, 4-benzyl biphenyl, 4,4'-dimethyl biphenyl and di-β-naphthylphenylene diamine.

Fillers used include clay, talc, kaolin, satin white, titanium oxide, calcium carbonate, magnesium carbonate, barium sulfate, magnesium silicate and aluminum silicate. In addition, dispersants used include sulfosuccinates such as sodium dioctylsulfosuccinate, sodium dodecylbenzene sulfonate, lauryl alcohol sulfate sodium salt and fatty acid salts. Colored image stabilizers used include salicylic acid derivatives, metal salts (particularly zinc salts) of oxynaphthoic acid derivatives, and other water-insoluble zinc compounds. Antioxidants used include 2,2'-methylene bis (4-6-tert-butylphenol),2,2'-methylene bis (4-ethyl-6-tert-butylphenol), 4,4'-propylmethylene bis (3-6-tert-butylphenol) and 4,4'-thiobis (2-tert-butyl-5-methylphenol). Desensitizing agents used include aliphatic higher alcohols, polyethylene glycol and guanidine derivatives. Adhesion preventive agents used include stearic acid, zinc stearate, calcium stearate, carnauba wax, paraffin wax and ester wax.

The fluoran compound of this invention is of course used for pressure sensitive copying paper, for which known method can be applied similar to those for known fluoran compounds: for example, a microcapsuled compound of this invention is dispersed with a proper dispersant and applied on paper to give a sheet with color former and separately a dispersion of developer is applied on paper to prepare a developer sheet. The two sheets thus prepared are combined to give pressure sensitive copying paper.

Developers used at the time are known agents, including inorganic acidic substances such as acid clay, activated clay, attapulgite, bentnite, colloidal silica, aluminum silicate, magnesium silicate, zinc silicate, tin silicate, calcined kaolin and talc; aliphatic carboxylic acids such as oxalic acid, maleic acid, tartaric acid, citric acid, succinic acid and stearic acid; aromatic carboxylic acids such as benzoic acid, p-tert-butyl benzoic acid, phthalic acid, gallic acid, salicylic acid, 3-isopropyl salicylic acid, 3-phenyl salicylic acid, 3-cyclohexyl salicylic acid, 3,5-di-tert-butyl salicylic acid, 3-methyl-5-benzyl salicylic acid, 3-phenyl-5-(2,2-dimethylbenzyl) salicylic acid, 3,5-di-(2-methylbenzyl) salicylic acid and 2-hydroxy-1-benzyl-3-naphtoic acid; metal salts with these aromatic carboxylic acids such as zinc, magnesium, aluminum and titanium; phenol resin developers such as p-phenylphenol-formalin resin and p-butylphenol-acetylene resin; and mixtures of these phenol resin developers and the said metal salts of aromatic carboxylic acids.

The benzoic acid derivative represented by the general formula (II), which is used for synthesis of fluoran compound represented by the general formula (I), is a new compound and easily synthesized by usual reaction such as shown by the following reaction formula:

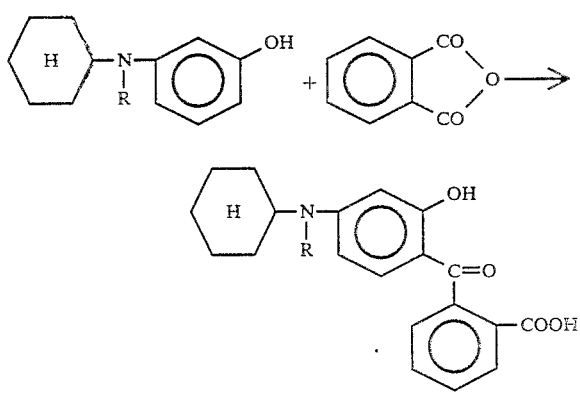

(where R is as defined above).

The reaction represented by the above reaction formula is attained by heating in an inactive organic solvent such as toluene, xylene, perchloroethylene or trichloroethylene, at a temperature between 80° C. and the boiling point of the solvent used, for 2 to 8 hours. Various methods are applicable to separate the intended product after the reaction is completed: for example, a NaOH solution is added to the reaction solution, deposited Na salt is filtrated to separate to neutralize with aqueous sulfuric-acid solution, and then the product is extracted with solvent.

Aminophenol derivatives which are materials to prepare benzoic acid derivatives represented by the general formula (II) can be prepared according to known methods.

BEST FORM TO EXECUTE THE INVENTION

Figure 1:
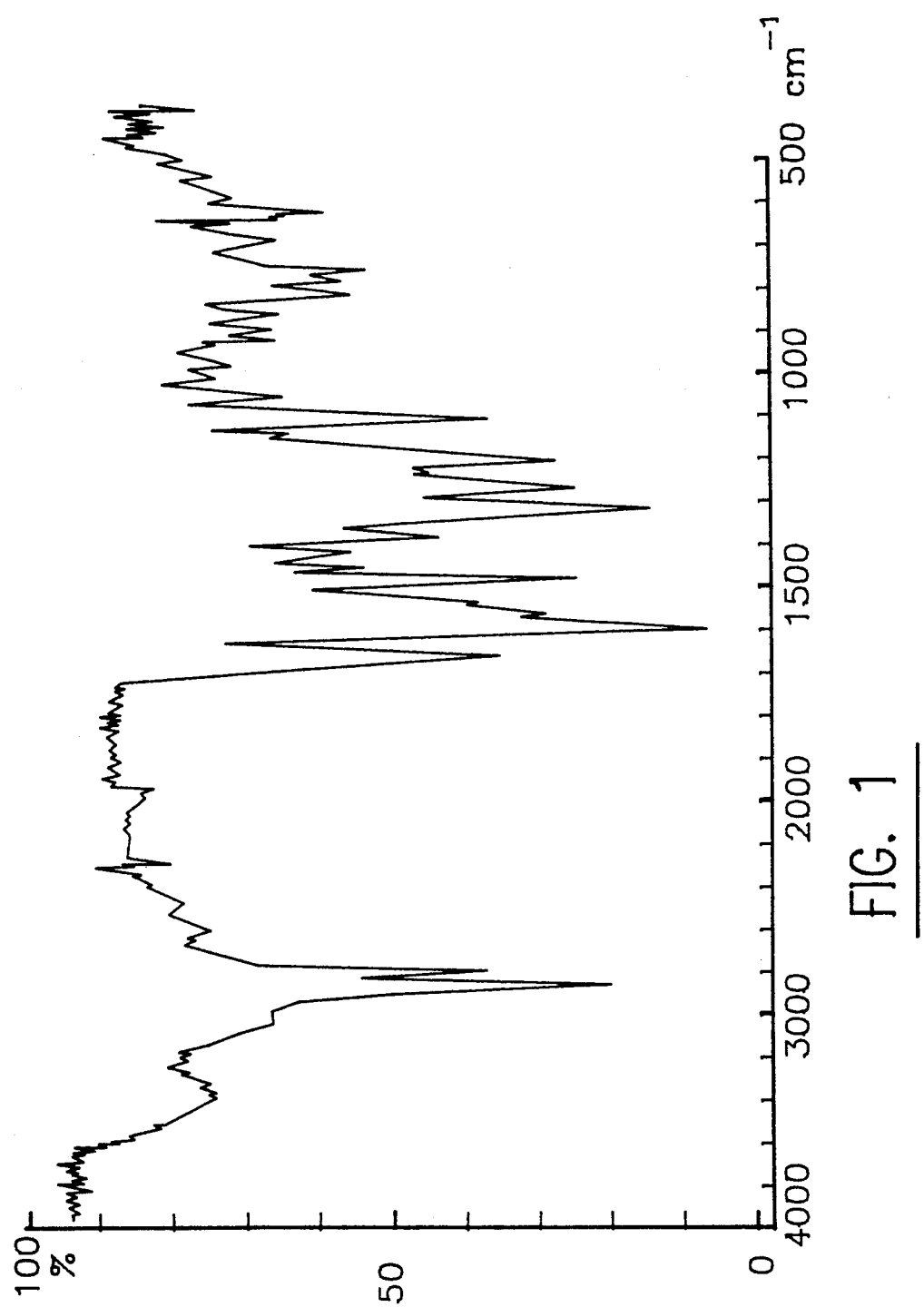
FIG. 1 is an IR absorption spectrum of 2-(4-N-cyclohexyl-n-nonylamino-2-hydroxybenzoyl) benzoic acid obtained in Example 6.
Figure 2:
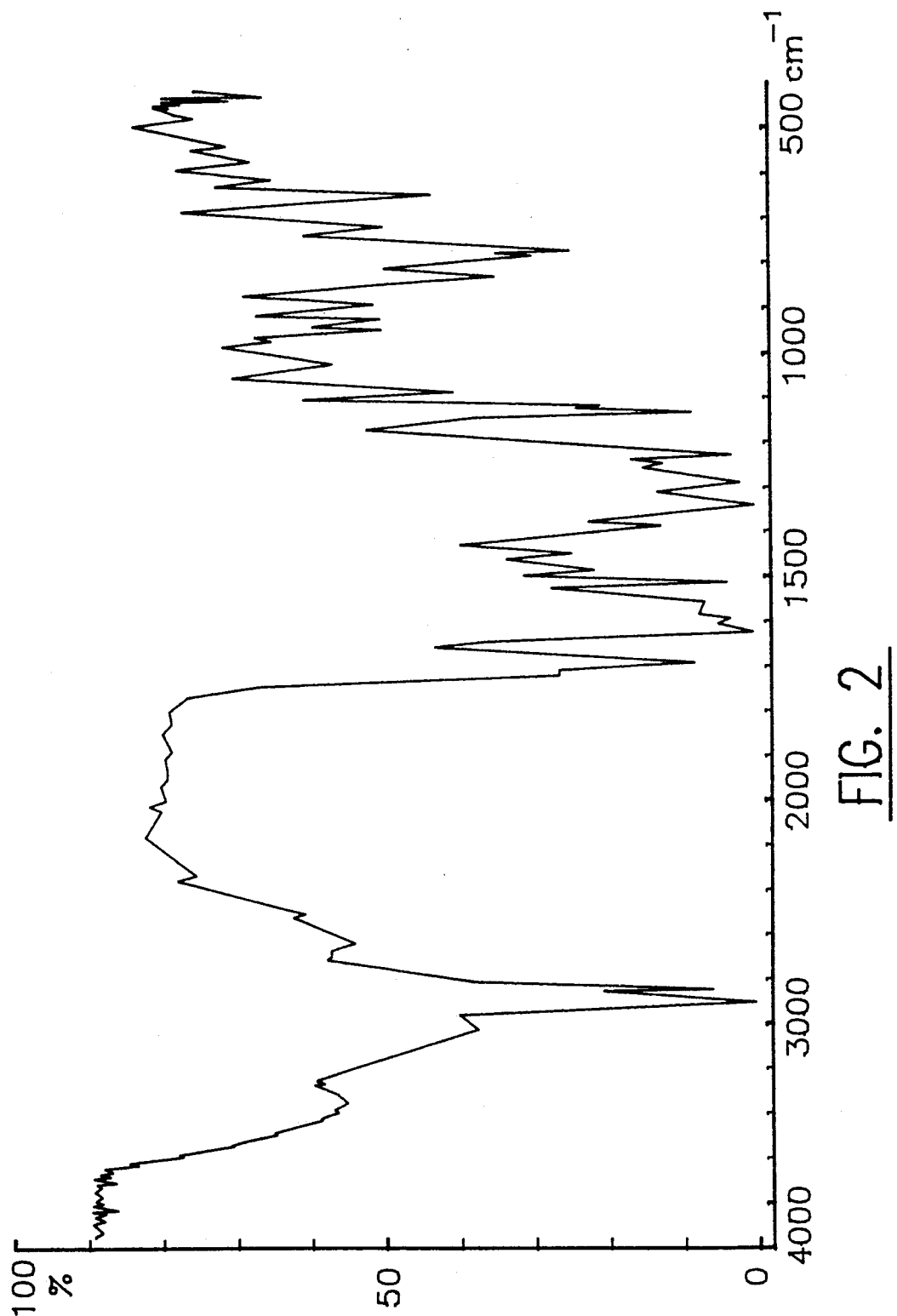
FIG. 2 is IR absorption spectrum of 2-(4-N-cyclohexyl-n-nonylamino-2-hydroxybenzoyl) benzoic acid obtained in Example 7. Both of the spectra have the absorption rate at the ordinate and wave number at the abscissa.
Figure 3:
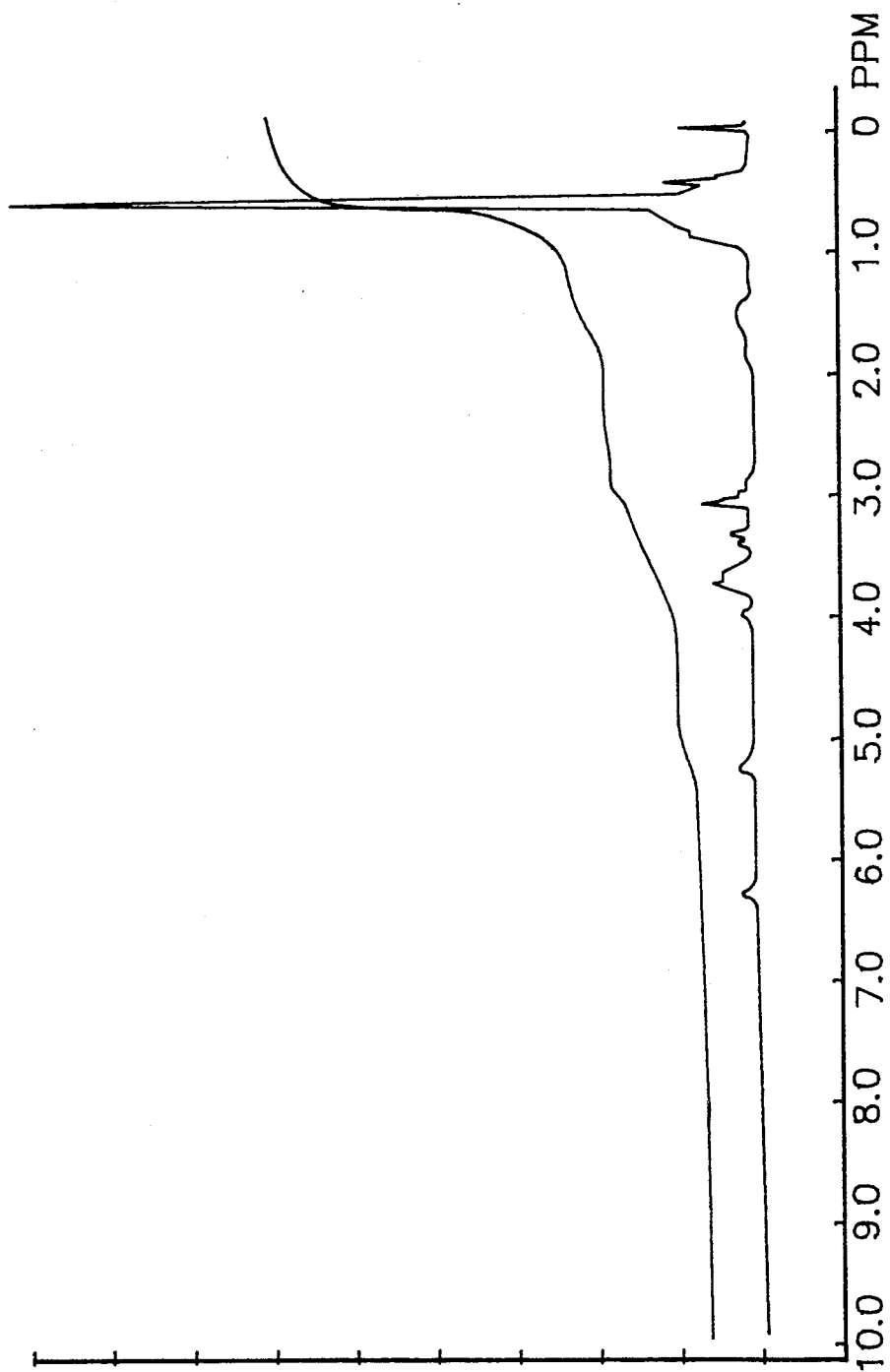
FIG. 3 is an NMR spectrum ($^1$H-NMR, 60 MHz, CDCl$_3$) of 2-(4-N-cyclohexyl-n-dodecylamino-2-hydroxybenzoyl) benzoic acid obtained in Example 7. The absorption intensity is at the ordinate and the intensity of magnetic field (PPM) at the abscissa.

The invention is further described in detail by reference to the following examples. The range of this invention is not limited at all by the following examples.

EXAMPLE 1

Example of flouran compound synthesis

To 81.3 g of concentrated sulfuric acid were added 17.0 g of 2-(4-N-cyclohexyl-n-nonylamino-2-hydroxybenzoyl) benzoate and 8.3 g of 2-methyl-4-methoxy diphenylamine. The resulting mixture was reacted with stirring at 15° to 25° C. for 24 hours. Then the reaction mixture was poured into 300 ml of ice water and deposited reaction product was filtrated to collet. The filtrated deposit was heated under reflux for an hour while stirring with 200 ml of water, 20 g aqueous solution of sodium hydroxide and 160 ml of toluene for extraction. The toluene layer was washed with water several times, filtrated and concentrated. The deposited crystal was filtrated. The obtained light yellow crystal was refluxed in n-hexane, cooled, filtrated and dried to give 16.0 g of 2-anilino-3-methyl-6-N-cyclohexyl-n-nonlaminofluoran (Compound No. 1) as white crystal with melting point of 159.2° to 160.5° C. This compound forms an addition product with toluene if deposited from toluene solvent, and heating the addition product in n-hexane under refux gives the said crystal free from toluene.

EXAMPLE 2

Example of fluoran compound synthesis

Example 1 was repeated nearly similarly except that 21.0 g of 2-(4-N-cyclohexyl-n-decylamino-2-hydroxybenzoyl) benzoate was used instead of 2-(4-N-cyclohexyl-n-nonylamino-2-hydroxybenzoyl) benzoate. The compound does not form an addition product with toluene. Therefore the toluene solution was concentrated to deposit crystal to filtrate to dry to give 11.7 g of 2-anilino-3methyl-6-N-cyclohexyl-n-decylaminofluoran (Compound No. 2) as white crystal with melting point of 135.2° 138.4° C.

EXAMPLE 3

Example of fluoran compound synthesis

Example 1 was repeated nearly similarly except that 20.0 g of 2-(4-N-cyclohexyl-n-dodecylamino-2-hydroxybenzoyl) benzoate was used instead of 2-(4-N-cyclohexyl-n-nonylamino-2-hydroxybenzoyl) benzoate. The compound does not form an addition product with toluene. Therefore the toluene solution was concentrated to deposit crystal to filtrate to dry to give 19.6 g of 2-anilino-3-methyl-6-N-cyclohexyl-n-dodecylaminofluoran (Compound No. 3) as white crystal with melting point of 114.5° to 117.4° C.

EXAMPLE 4

Heat sensitive recording paper

Adjustment of suspension and preparation of heat sensitive recording paper

* Dye suspension: 3.5 g of fluoran compound, 15.0 g of clay, 41.5 g of 15% polyvinyl alcohol aqueous solution, 40.0 g of water
* Developer suspension: 10.5 g of developer, 8.0 g of clay, 41.5 g of 15% polyvinyl alcohol aqueous solution, 40.0 g of water Each of the suspension with the said composition was placed in a polyethylene bottle together with 150 g of glass beads (diameter: 1–1.5 mm). The bottles were hermetically stoppered and each suspension was ground by paint conditioner of Red Devil Co for several hours for the preparation of dye and developer suspensions respectively. The dye and developer suspensions were mixed at a ratio of 1:1 to give an application solution. This application solution was applied on white paper by using wire rod No. 12, and the paper was dried to give heat sensitive paper.

According to the above procedure, heat sensitive recording papers I, II and III with the following fluoran compound and developer were prepared.

| Heat sensitive recording paper | Fluoran compound | Developer |
| --- | --- | --- |
| I | No. 1 | Bisphenol A |
| II | No. 2 | Bisphenol A |
| III | No. 3 | Bisphenol A |

These heat sensitive recording papers were each heated the two sides at 150° C. by using a Dry Heating Tester (produced by Kishino Science Machinery Co., ltd.) in order to color a part of the paper. The part colored black clearly.

The heat sensitive recording papers with colored and non-colored portions were examined by storability tests consisting of humidity/heat resistance tests (50° C., relative humidity: 90%, 24 hours) and light resistance test (sunlight, 20 hour exposure). Both of the background and colored portion of the heat sensitive recording paper showed almost no difference between before and after the test.

Furthermore, the background of these papers before and after the test was measured by using Macbeth reflection densitometer Model RD-514. The results are summarized in Table 2 with those for Comparative Example 1.

COMPARATIVE EXAMPLE 1

Example 4 was repeated to prepare heat sensitive recording paper IV except that 2-anilino-3-methyl-6-N-cyclohexyl-n-octylaminofluoran was used instead of the compound of this invention in Example 4.

In addition, according to the procedure of Example 4, a part of the paper was heated the two sides to color, tested for the storability similar to Example 4, and measured the background by Macbeth reflection densitometer. The results are shown in Table 2 together with those of Example 4.

TABLE 2

| Heat sensitive recording paper No. | Background Before test | Humid/heat resistance | Light resistance |
|---|---|---|---|
| I | 0.07 | 0.11 | 0.19 |
| II | 0.06 | 0.10 | 0.17 |
| III | 0.06 | 0.11 | 0.17 |
| IV* | 0.07 | 0.27 | 0.38 |

*Comparative example

When the measured values of the papers before and after the tests by Macbeth reflection densitometer are compared in the above table, heat sensitive recording paper has better storability with smaller difference in the measured values: The above results indicate that the fluoran compounds of this invention whose alkyl group represented by R has 9 to 12 carbon atoms has clearly less fluctuation and is thus a coloring dye with excellent storability, when compared with known fluoran compound with alkyl group having 8 carbon atoms.

EXAMPLE 5

Pressure sensitive copying paper 2.0 g of Compound No. 2 synthesized in Example 2 was mixed with 25.0 g of alkyldiphenyl methane (Nippon Petroleum Chemical Co., Ltd. "Hisol SAS296") and 18.0 g of diisopro pylnaphathalene (Kureha Chemical Industry "KMC-113"), and heated to dissolve (Solution A).

Meanwhile, 15.0 g of 10% aqueous solution of sulfonate modified polyvinyl alcohol (the Nippon Synthetic Chemical Industry Co., Ltd. "Gosenol CSK-50"), 34 g of pure water, 7.5 g of 10% aqueous solution of ethylene-maleic anhydride copolymer (Monsanto "EMA-31"), 2.5 g of urea and 0.25 g of resorcinol were mixed and the pH was adjusted to 3.4 by using 20% sodium hydroxide (Solution B).

Solution A was added to Solution B to make an emulsion by using a homomixer, to which 7.0 g of 35% aqueous formalin solution was added to keep stirring for an hour at temperatureof 60° to 65° C. After cooled to 40° C. 28% aqueous ammonia was added to adjust the pH to 7.5 to give a microcapsule dispersion.

27.0 g of this dispersion, 3.5 g of wheat starch, 3.5 g of 8% aqueous wheat starch solution and 34.0 ml of water were mixed to prepare an application solution.

The obtained application solution was applied on white paper by using wire bar No. 12, and the parer was dried to prepare top paper of pressure sensitive copying paper.

The solution applied side of the obtained top paper was each placed on the solution applied side of each of bottom paper prepared by applying phenol-formalin in resin to dry and clay bottom paper (Fuji Photo Flim). Each obtained paper was typed by typewriter to color.

As the result, clear black printed characters appeared on the two bottom papers.

EXAMPLE 6

Example of synthesis of benzoic acid derivative 34.7 g of m-(N-cyclohexyl-n-decylamino) phenol and 15.5 g of phthalic anhydride were added to 60 ml of toluene to stir for 6 hours under refluxing. 20 g of 4% aqueous NaOH solution was added and heated under reflux. The resulting mixture was left still to separate layers. The toluene layer was washed with 20 ml of water, to which 5.1 g of flake sodium hydroxide and 36 ml of water were added to stir. After cooled to room temperature, the deposited crystal (Na salt) was filtrated. This crystal was washed with acetone, then neutralized with 50% sulfuric acid in 60 ml of water and 60 ml of toluene, and adjusted to pH 4. After heated to reflux, the solution was separated to layers, the toluene layer was washed with 20 ml of warm water, and then dried under reduced pressure to give 25 g of the glutenous substance. This substance was proved to be a single substance by thin layer chromatography (developing solvents: chloroform 9, toluene 3, methanol 1.5). It has absorptions of OH (3400 $cm^{-1}$), $CH_2$ (2925, 2850 $cm^{-1}$) and C=0 (1700 $cm^{-1}$) on the IR absorption specturm. Thus the substance was proved to be the intended product of 2-(4-N-cyclohexyl-n-decylamino-2-hydroxybenzoyl) benzoic acid.

EXAMPLE 7

Example of synthesis of benzoic acid derivative

Example 6 was repeated except using m-(N-cyclohexyl-n-nonylamino) phenol instead of n-(N-cyclohexyl-n-decylamino) phenol. Glutenous 2-(4-N-cyclohexyl-n-nonylamino-2-hydroxybenzoyl) benzoic acid was obtained.

EXAMPLE 8

Example of synthesis of benzoic acid derivative

Example 6 was repeated except using m-(N-cyclohexyl-n-dodecylamino) phenol instead of n-(N-cyclohexyl-n-decylamino) phenol. Glutenous 2-(4-N-cyclohexyl-n-dodecylamino-2-hydroxybenzoyl) benzoic acid was obtained.

POSSIBILITY OF INDUSRTRIAL APPLICATIONS

The new flouran compounds of this invention have melting point as low as in a range of 115° to 160° C., thereby being very superior coloring dyes for heat sensitive recording paper in which the melting point affects the coloring sensitivity. In addition, the compounds are excellent instorability in a way that the background less stained when compared with conventional fluorn compounds. They are also advantageous to apply to pressure sensitive copying paper because of excellent solubility in organic solvents.

The benzoic acid derivatives of this invention, when used as material compounds, give various fluoran compounds extremely good as coloring dyes, being useful as synthetic intermediates.

What is claimed is:

1. A coloring recording material which comprises containing one or more fluoran compounds represented by the general formula (I)

[Structure I: diagram showing fluoran-type compound with cyclohexyl-N(R)- group, O bridge, CH3, NH-phenyl, and lactone C=O]

(where R is an alkyl group having 9 to 12 carbon atoms), as coloring dyes.

2. A benzoic acid derivative represented by the general formula (II)

[Structure II: diagram showing cyclohexyl-N(R)- substituted phenyl with OH, C=O linked to phenyl-COOH]

(where R is an alkyl group having 9 to 12 carbon atoms.

* * * * *